United States Patent
Yi et al.

(10) Patent No.: US 11,654,094 B2
(45) Date of Patent: May 23, 2023

(54) COMPOSITION COMPRISING BENZOIC ACID AMIDE COMPOUND AND CYCLODEXTRIN SOLUBILIZING AGENT

(71) Applicant: AMOREPACIFIC CORPORATION, Seoul (KR)

(72) Inventors: Chang-geun Yi, Yongin-si (KR); Suil Kim, Yongin-si (KR); Sung Il Park, Yongin-si (KR); Hong-ju Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 189 days.

(21) Appl. No.: 16/499,729

(22) PCT Filed: Mar. 26, 2018

(86) PCT No.: PCT/KR2018/003536
§ 371 (c)(1),
(2) Date: Sep. 30, 2019

(87) PCT Pub. No.: WO2018/182257
PCT Pub. Date: Oct. 4, 2018

(65) Prior Publication Data
US 2021/0093532 A1 Apr. 1, 2021

(30) Foreign Application Priority Data
Mar. 31, 2017 (KR) .......................... 10-2017-0042192

(51) Int. Cl.
| | | |
|---|---|---|
| A61K 8/42 | (2006.01) | |
| A61K 8/02 | (2006.01) | |
| A61K 8/19 | (2006.01) | |
| A61K 8/31 | (2006.01) | |
| A61K 8/34 | (2006.01) | |
| A61K 8/37 | (2006.01) | |
| A61K 8/41 | (2006.01) | |
| A61K 8/67 | (2006.01) | |
| A61K 8/73 | (2006.01) | |
| A61K 8/81 | (2006.01) | |
| A61K 8/92 | (2006.01) | |
| A61Q 5/12 | (2006.01) | |
| A61Q 19/00 | (2006.01) | |

(52) U.S. Cl.
CPC .............. *A61K 8/42* (2013.01); *A61K 8/0212* (2013.01); *A61K 8/19* (2013.01); *A61K 8/31* (2013.01); *A61K 8/34* (2013.01); *A61K 8/345* (2013.01); *A61K 8/375* (2013.01); *A61K 8/41* (2013.01); *A61K 8/678* (2013.01); *A61K 8/73* (2013.01); *A61K 8/738* (2013.01); *A61K 8/8147* (2013.01); *A61K 8/92* (2013.01); *A61K 8/922* (2013.01); *A61Q 5/12* (2013.01); *A61Q 19/007* (2013.01)

(58) Field of Classification Search
CPC ...... A61K 2800/49; A61K 47/40; A61K 8/41; A61K 9/0014
See application file for complete search history.

(56) References Cited

U.S. PATENT DOCUMENTS

| | | | |
|---|---|---|---|
| 4,727,064 A | * | 2/1988 | Pitha .................... A61K 31/565 106/205.01 |
| 8,697,151 B2 | | 4/2014 | Contet-Audonneau et al. |
| 9,018,236 B2 | | 4/2015 | Trumbore et al. |
| 9,216,145 B2 | | 12/2015 | Rabe et al. |
| 9,254,251 B2 | | 2/2016 | Joo et al. |
| 2011/0182835 A1 | * | 7/2011 | Caetano .................... A61K 8/37 424/60 |
| 2013/0251644 A1 | | 9/2013 | Majhi et al. |
| 2014/0234241 A1 | * | 8/2014 | Joo ........................ A61Q 19/02 424/62 |
| 2018/0116933 A1 | | 5/2018 | Joo et al. |

FOREIGN PATENT DOCUMENTS

| | | |
|---|---|---|
| CN | 103702977 A | 4/2014 |
| CN | 104147602 A | 11/2014 |
| CN | 104363893 A | 2/2015 |
| JP | 2011-528708 A | 11/2011 |
| JP | 2015-120716 A | 7/2015 |
| KR | 10-2005-0039573 A | 4/2005 |
| KR | 10-2013-0015954 A | 2/2013 |
| KR | 10-2013-0107616 A | 10/2013 |
| KR | 10-2014-0134712 A | 11/2014 |
| KR | 10-1502533 B1 | 3/2015 |
| KR | 10-1604063 B1 | 3/2016 |
| KR | 10-2016-0116941 A | 10/2016 |
| WO | 2005/040106 A1 | 5/2005 |
| WO | 2008/070670 A2 | 6/2008 |
| WO | 2009/066955 A2 | 5/2009 |
| WO | 2009/140743 A2 | 11/2009 |

(Continued)

OTHER PUBLICATIONS

Klang et al (International Journal of Pharmaceutics, 2012, vol. 423, pp. 535-542) (Year: 2012).*
Wang et al (J. Incl. Phenom. Macrocycl. Chem., 2014, vol. 78, pp. 145-150) (Year: 2014).*
International Search Report from PCT/KR2018/003536, dated Jun. 28, 2018.

(Continued)

*Primary Examiner* — Mark V Stevens
(74) *Attorney, Agent, or Firm* — Merchant & Gould P.C.

(57) ABSTRACT

The present specification relates to a composition for external application to skin with improved solubility and feeling during use, comprising a benzoic acid amide compound, an isomer thereof, a pharmaceutically acceptable salt thereof, a hydrate thereof or a solute that is a solvate thereof, and a first cyclodextrin solubilizing agent.

18 Claims, 3 Drawing Sheets

(56) References Cited

FOREIGN PATENT DOCUMENTS

| WO | 2010/010510 A2 | 1/2010 |
|---|---|---|
| WO | 2013/033520 A1 | 3/2013 |
| WO | 2013/142249 A1 | 9/2013 |
| WO | 2016/159640 A2 | 10/2016 |
| WO | 2018/062958 A1 | 4/2018 |

OTHER PUBLICATIONS

Written Opinion from PCT/KR2018/003536, dated Jun. 28, 2018.

Chang Seok Lee et al., "A novel adamantyl benzylbenzamide derivative, AP736, suppresses melanogenesis through the inhibition of cAMP-PKA-CREB-activated microphthalmia-associated transcription factor and tyrosinase expression," Experimental Dermatology, 22, pp. 748-774 (2013).

Heung Soo Baek et al., "Adamantyl N-benzylbenzamide: New series of depigmentation agents with tyrosinase inhibitory activity," Bioorganic & Medicinal Chemistry Letters, 22, pp. 2110-2113 (2012).

Heung Soo Baek et al., "Whitening Effects of Adamantyl Benzamide Derivatives," J. Soc. Cosmet. Scientists Korea, vol. 39, No. 2, pp. 127-132 (Jun. 2013).

Ushakova L.S. "Preparation, research and use of inclusion complexes of cortisone acetate, dexamethasone and sinaflan with cyclodextrins", Candidate of pharm. sciences dissertation.—Pyatigorsk: pp. 3, 9 (1996)—** described in English Translation of Russian Office Action dated May 14, 2021.

Russian Patent Application No. 2019134650/04(068285), dated May 14, 2021.

P. Jarho et al., "Hydroxyprapyl-β-cyclodextrin and its combination with hydroxypropyl-methylcellulose increases aqueous solubility of Δ9-tetrahydrocannabinol", Life Sciences, vol. 63, No. 26: 381-384 (1998).

N. Zerrouk et al., "Influence of cyclodextrins and chitosan, separately or in combination, on glyburide solubility and permeability", European Journal of Pharmaceutics and Biopharmaceutics, vol. 62, No. 3: 241-246 (2006).

Search Report for European Patent Application No. 18776715.7, dated Feb. 8, 2021.

Kong Deog Hong et al., "3D-QSAR study of adamantyl N-benzylbenzamides as melanogenesis inhibitors" Bioorganic & Medicinal Chemistry Letters, 2014, vol. 24, pp. 667-673.

Jutima Boonleang et al., "Effect of hydroxypropyl-β-cyclodextrin on the stability of cisapride in oral suspensions", Songklanakarin J. Sci. Technol., 32(6): 605-611 (2010).

Office Action for Korean Patent Application No. 10-2017-0042192 (dated Sep. 1, 2021).

Notice of Allowance for Korean Patent Application No. 1020170042192. (dated Jan. 20, 2022).

Ju-fen et al., "Progress on the Techniques for Enhancing Aqueous Solubility of Water Insoluble Drugs for Parenteral Delivery", Pharmaceutical Biotechnology, 2014, 21(3): 253-259.

Kang et al., Progress in Research and Application of Cyclodextrin in Marketed Drug Formulations, Progress in Pharmaceutical Sciences, 2016, 40(7): 483-489.

Office Action for Corresponding CN Application No. 201880036680.9 dated Jul. 8, 2022. (7 pages).

\* cited by examiner

COMPOSITION COMPRISING BENZOIC ACID AMIDE COMPOUND AND CYCLODEXTRIN SOLUBILIZING AGENT

This application is a National Stage Application of International Application No. PCT/KR2018/003536, filed 26 Mar. 2018, which claims benefit of Ser. No. 10-2017-0042192, filed 31 Mar. 2017 in Korea and which applications are incorporated herein by reference. To the extent appropriate, a claim of priority is made to each of the above disclosed applications.

TECHNICAL FIELD

The present disclosure relates to a composition for external application to the skin comprising a solute which is a benzoic acid amide compound, an isomer thereof, a pharmaceutically acceptable salt thereof, a hydrate thereof or a solvate thereof; and a cyclodextrin solubilizer, and which has improved solubility.

BACKGROUND ART

Melanin protects skin organs beneath the dermis by blocking UV at the epidermis and also protects the skin by scavenging free radicals. Also, melanin is the primary determinant of skin color and is the cause of pigmentation such as melasma, freckles, nevus, etc. when existing in excess. Melanin is produced by melanocytes, which are found in the basal layer of the skin. It is known that the production of melanin is promoted by stimuli such as UV or inflammation. Accordingly, the melanin production can be reduced by decreasing external stimulation, blocking signal transduction or inhibiting synthesis of the melanin-producing enzyme tyrosinase or inhibiting activity thereof. Until now, kojic acid, hydroquinone, arbutin, azelaic acid, aloesin, 4-butylresorcinol, resveratrol, ceramide, sphingosine-1-phosphate, sphingosylphosphorylcholline, etc. are known to be able to regulate melanin production by promoting tyrosinase breakdown or regulating glycosylation. However, these substances are not used widely due to unsatisfactory skin whitening effects and low stability as well as skin irritation. Recently, benzoic acid amide materials having an excellent whitening effect and less side effects have been studied.

*Broussonetia kazinoki* has traditionally been used as a raw material for producing Korean handmade paper. From the fact that people making Korean handmade paper have white and fine hands, it has been predicted that *Broussonetia kazinoki* would have a skin whitening effect. Accordingly, scientific studies have been conducted, which showed that roots of *Broussonetia kazinoki* contain kazinol, which is an ingredient with an excellent whitening effect. "*Broussonetia kazinoki* extract" was also notified as a functional cosmetic raw material by the Korean Ministry of Food and Drug Safety. Accordingly, the structure of kazinol, which is present in *Broussonetia kazinoki* and has a whitening effect, was analyzed by molecular modeling to investigate the functional groups of kazinol which exhibit a whitening effect. In particular, it is difficult to use kazinol F as a single ingredient, despite its excellent whitening effect, because it is present in a trace amount in *Broussonetia kazinoki* and has a structure easily decomposed by temperature.

Dihydroxybenzyl adamantnyldimethoxybenzamide (DBAB) is a compound newly developed based on the quantitative structure-activity relationship (QSAR) and 3D-QSAR analysis of 100 types of derivatives obtained by simulating the structure of the trace element of *Broussonetia kazinoki*, kazinol F, and by considering efficacy, stability and manufacturability. It was found that this compound exhibits a new whitening effect by the following mechanism: The compound reduces the expression of MITF through the cAMP-PKA-CREB signal pathway and consequently inhibits the activity of tyrosinase, TRP-1, and TRP-2, which are the major proteins involved in melanin synthesis and regulated by MITF, thus inhibiting melanin synthesis. This effect was verified through cell and artificial skin tests.

However, there has been no research to improve the solubility of compositions containing a benzoic acid amide material. The present inventors have conducted a study on a composition of a benzoic acid amide material having improved solubility, leading to the present invention.

SUMMARY OF INVENTION

Technical Problem

In view of the above problems, the present inventors have made studies on a composition comprising a solubilizer for improving the solubility of a composition which comprises a benzoic acid amide compound, leading to the present invention.

One aspect of the present invention is to provide a composition which improves the solubility of a benzoic acid amide compound, yet which does not adversely affect the feeling of use.

Solution to Problem

One aspect of the present invention provides a composition for external application to the skin comprising a solute which is a compound represented by the following Formula 1, an isomer thereof, a pharmaceutically acceptable salt thereof, a hydrate thereof or a solvate thereof; and a first solubilizer which is cyclodextrin:

[Formula 1]

In Formula 1, $R_1$, $R_3$ and $R_4$ are each independently selected from the group consisting of hydrogen, hydroxy, $C_1$ to $C_5$ alkoxy, $C_3$ to $C_6$ cycloalkoxy, aryloxy and $C_1$ to $C_5$ haloalkoxy, $R_2$ is selected from the group consisting of hydrogen, $C_1$ to $C_5$ alkyl, $C_3$ to $C_6$ cycloalkyl, aryl and $C_1$ to $C_5$ haloalkyl, and n is an integer selected from 1 to 5.

In one aspect of the present invention, $R_1$, $R_3$ and $R_4$ of Formula 1 may be each independently selected from the group consisting of hydrogen, hydroxy, $C_1$ to $C_3$ alkoxy, $C_3$ to $C_6$ cycloalkoxy, aryloxy and $C_1$ to $C_3$ haloalkoxy, $R_2$ may be selected from the group consisting of hydrogen, $C_1$ to $C_3$ alkyl, $C_3$ to $C_6$ cycloalkyl, aryl and $C_1$ to $C_3$ haloalkyl, and n may be an integer selected from 1 to 3.

In one aspect of the present invention, the solute may be a compound selected from the group consisting of:

5-adamantan-1-yl-N-[2-(3,4-dihydroxyphenyl)-ethyl]-2,4-dihydroxy-benzoic acid amide,
5-adamantan-1-yl-N-[2-(3,4-dihydroxyphenyl)-ethyl]-2-hydroxy-4-methoxy-benzoic acid amide,
5-adamantan-1-yl-N-(3,4-dihydroxybenzyl)-2,4-dihydroxy-benzoic acid amide,
5-adamantan-1-yl-N-(3,4-dihydroxybenzyl)-2-hydroxy-4-methoxy-benzoic acid amide,
5-adamantan-1-yl-2,4-dihydroxy-N-[2-(4-hydroxyphenyl)-ethyl]-benzoic acid amide,
5-adamantan-1-yl-2-hydroxy-N-[2-(4-hydroxyphenyl)-ethyl]-4-methoxy-benzoic acid amide,
5-adamantan-1-yl-N-[2-(4-hydroxyphenyl)-ethyl]-2,4-dimethoxy-benzoic acid amide,
5-adamantan-1-yl-N-(2,4-dihydroxybenzyl)-2,4-dihydroxy-benzoic acid amide,
5-adamantan-1-yl-N-(2,4-dihydroxybenzyl)-2-hydroxy-4-methoxy-benzoic acid amide,
5-adamantan-1-yl-N-(2,4-dihydroxybenzyl)-2,4-dimethoxy-benzoic acid amide,
3-adamantan-1-yl-N-(3,4-dihydroxybenzyl)-4-hydroxy-benzoic acid amide,
3-adamantan-1-yl-N-(3,4-dihydroxybenzyl)-4-methoxy-benzoic acid amide,
3-adamantan-1-yl-N-[2-(3,4-dihydroxyphenyl)-ethyl]-4-hydroxy-benzoic acid amide,
3-adamantan-1-yl-N-[2-(3,4-dihydroxyphenyl)-ethyl]-4-methoxy-benzoic acid amide,
3-adamantan-1-yl-4-hydroxy-N-[2-(4-hydroxyphenyl)-ethyl]-benzoic acid amide,
3-adamantan-1-yl-N-[2-(4-hydroxyphenyl)-ethyl]-4-methoxy-benzoic acid amide,
3-adamantan-1-yl-N-(2,4-dihydroxybenzyl)-4-hydroxy-benzoic acid amide,
3-adamantan-1-yl-N-(2,4-dihydroxybenzyl)-4-methoxy-benzoic acid amide,
5-adamantan-1-yl-N-(2,5-dimethoxybenzyl)-2,4-dihydroxy-benzoic acid amide,
5-adamantan-1-yl-N-(2,5-dimethoxybenzyl)-2,4-dihydroxy-benzoic acid amide,
5-adamantan-1-yl-N-(3,5-dimethoxybenzyl)-2,4-dihydroxy-benzoic acid amide and
5-adamantan-1-yl-2,4-dihydroxy-N-(3-hydroxy-5-methoxybenzyl)-benzoic acid amide, an isomer thereof, a pharmaceutically acceptable salt thereof, a hydrate thereof or a solvate thereof.

In one aspect of the present invention, the solute may be 5-adamantan-1-yl-N-(2,4-dihydroxybenzyl)-2,4-dimethoxy-benzoic acid amide.

In one aspect of the present invention, the cyclodextrin may be at least one of α-cyclodextrin, β-cyclodextrin, γ-cyclodextrin, hydroxypropyl-α-cyclodextrin, hydroxypropyl-β-cyclodextrin (HP-β-CD) and hydroxypropyl-γ-cyclodextrin.

In one aspect of the present invention, the weight ratio of the solute and the first solubilizer may be 1:0.1 to 100.

In one aspect of the present invention, the first solubilizer may be hydroxypropyl-β-cyclodextrin, and the weight ratio of the solute and the first solubilizer may be of 1:2 to 100.

In one aspect of the present invention, the first solubilizer may comprise hydroxypropyl-β-cyclodextrin and γ-cyclodextrin in a weight ratio of 1:0.1 to 10, and the weight ratio of the solute and the first solubilizer may be in 1:0.1 to 100.

Another aspect of the present invention provides a composition for external application to the skin further comprising a pH adjuster.

In another aspect of the present invention, the pH adjuster may be at least one of potassium hydroxide (KOH), calcium hydroxide (Ca(OH)$_2$), sodium carbonate (Na$_2$CO$_3$), potassium carbonate (K$_2$CO$_3$), sodium bicarbonate (NaHCO$_3$), lithium hydroxide (LiOH), citric acid, lactic acid, 2-aminobutanol, acetic acid, acetyl mandelic acid, adipic acid, aluminum hydroxide oxide, aluminum triformate, aminoethyl propanediol, aminomethyl propanediol, aminomethyl propanol, aminopropanediol, ammonia, ammonium bicarbonate, ammonium carbamate, ammonium carbonate, ammonium glycolate, ammonium hydroxide, ammonium phosphate, ascorbic acid, azelaic acid, babassu acid, benzylic acid, benzoic acid, bis-hydroxyethyl tromethamine, butyl diethanolamine, butylethanolamine, calcium citrate, calcium dihydrogen phosphate, calcium glycinate, calcium oxide, camphor sulfonic acid, chloroacetic acid, copper glycinate, dibutyl ethanolamine, diethanolamine, diethanolamine bisulfate, diisopropanolamine, diisopropylamine, dimethyl isopropanolamine, dimethyl MEA, dioleoyl edetolmonium methosulfate, dioleyl phosphate, dipotassium phosphate, dipropylenetriamine, disodium fumarate, disodium phosphate, disodium pyrophosphate, disodium tartrate, ethanolamine, ethanolamine HCl, ethyl ethanolamine, formic acid, fumaric acid, galacturonic acid, geranic acid, glucoheptonic acid, glucosamine HCl, glucuronic acid, glutaric acid, glycolic acid, glyoxylic acid, guanidine carbonate, hydrobromic acid, hydrochloric acid, imidazole, isopropanolamine, isopropylamine, ketoglutaric acid, lactobionic acid, lithium carbonate, magnesium carbonate, magnesium carbonate hydroxide, magnesium glycinate, magnesium hydroxide, magnesium oxide, maleic acid, malic acid, malonic acid, maltobionic acid, metaphosphoric acid, methoxy PEG-100/polyepsilon caprolactone ethylhexanoate, methoxy PEG-100/polyepsilon caprolactone palmitate, methoxy PEG-114/polyepsilon caprolactone, methylethanolamine, methylglucamine, morpholine, morpholinopropane sulfonic acid, oxalic acid, p-anisic acid, pentapotassium triphosphate, pentasodium triphosphate, phenolsulfonphthalein, phosphoric acid, potassium bicarbonate, potassium biphthalate, potassium borate, potassium citrate, potassium magnesium aspartate, potassium oxide, potassium phosphate, potassium tartrate, propionic acid, quinic acid, ribonic acid, sebacic acid, sesquiethoxytriethanolamine, sodium aluminate, sodium anisate, sodium arachidate, sodium bisulfate, sodium borate, sodium calcium boron phosphate, sodium calcium copper phosphate, sodium calcium zinc phosphate, sodium cinnamate, sodium citrate, sodium cyanate, sodium fumarate, sodium glycolate, sodium hydroxide, sodium oxide, sodium sesquicarbonate, sodium silicate, sodium succinate, sodium trimetaphosphate, sodium tungstate antimonate, strontium hydroxide, succinic acid, sulfonated styrene/DVB crosspolymer, sulfuric acid, tartaric acid, TEA-diricinoleate/IPDI copolymer, tetrapotassium pyrophosphate, tetrasodium pyrophosphate, triethanolamine, triisopropanolamine, trisodium phosphate, trisodium sulfosuccinate, tromethamine, vinegar, zinc carbonate hydroxide, zinc glycinate, and zinc magnesium aspartate.

In another aspect of the present invention, when the composition for external application to the skin has a pH of 2 or higher, the weight ratio of the solute and the first solubilizer may be 1:0.1 to 50.

In another aspect of the present invention, when the composition for external application to the skin has a pH of 2 to 10, the weight ratio of the solute and the first solubilizer may be 1:4 to 12, and the first solubilizer may be hydroxypropyl-β-cyclodextrin.

In one or more aspects of the present invention, the content of the solute may be 0.01 to 20% by weight based on the total weight of the composition.

In one or more aspects of the present invention, the composition may further comprise a second solubilizer which is at least one selected from the group consisting of xanthan gum, hydroxypropyl methylcellulose, sodium polyacrylate, sodium magnesium silicate, hydroxyethyl acrylate/sodium acryloyldimethyl taurate copolymer, polyacrylate-13/polyisobutene/polysorbate-20, PEG-240/HDI copolymer bis-decyltetraceth-20 ether and magnesium aluminum silicate.

In one or more aspects of the present invention, the composition may further comprise a third solubilizer which is at least one of diethylene glycol monoethyl ether, methyl gluceth, glyceryl ether, polyethylene glycol, and polyethylene glycol/polypropylene glycol copolymer.

In another aspect of the present invention, the composition for external application to the skin is provided as a composition for skin whitening.

In another aspect of the present invention, the composition for external application to the skin is provided as a pharmaceutical or cosmetic composition.

Advantageous Effects of Invention

In the composition according to one aspect of the present invention, the solute which is a benzoic acid amide compound, an isomer thereof, a pharmaceutically acceptable salt thereof, a hydrate thereof or a solvate thereof has excellent solubility.

In the composition according to one aspect of the present invention, a benzoic acid amide compound as a solute does not precipitate.

When applied to the skin, the composition according to one aspect of the present invention has excellent solubility and excellent feeling of use.

DESCRIPTION OF EMBODIMENTS

Embodiments

Hereinafter, the present invention will be described in detail.

One aspect of the present invention provides a composition for external application to the skin comprising a solute which is a compound represented by the following Formula 1, an isomer thereof, a pharmaceutically acceptable salt thereof, a hydrate thereof or a solvate thereof; and a first solubilizer which is cyclodextrin:

[Formula 1]

In Formula 1, $R_1$, $R_3$ and $R_4$ are each independently selected from the group consisting of hydrogen, hydroxy, $C_1$ to $C_5$ alkoxy, $C_3$ to $C_6$ cycloalkoxy, aryloxy and $C_1$ to $C_5$ haloalkoxy, $R_2$ is selected from the group consisting of hydrogen, $C_1$ to $C_5$ alkyl, $C_3$ to $C_6$ cycloalkyl, aryl and $C_1$ to $C_5$ haloalkyl, and n is an integer selected from 1 to 5.

In one aspect of the present invention, $R_1$, $R_3$ and $R_4$ of Formula 1 may be each independently selected from the group consisting of hydrogen, hydroxy, $C_1$ to $C_3$ alkoxy, $C_3$ to $C_6$ cycloalkoxy, aryloxy and $C_1$ to $C_3$ haloalkoxy, $R_2$ may be selected from the group consisting of hydrogen, $C_1$ to $C_3$ alkyl, $C_3$ to $C_6$ cycloalkyl, aryl and $C_1$ to $C_3$ haloalkyl, and n may be an integer selected from 1 to 3.

In one aspect of the present invention, the solute may be a compound selected from the group consisting of:

5-adamantan-1-yl-N-[2-(3,4-dihydroxyphenyl)-ethyl]-2,4-dihydroxy-benzoic acid amide, 5-adamantan-1-yl-N-[2-(3,4-dihydroxyphenyl)-ethyl]-2-hydroxy-4-methoxy-benzoic acid amide, 5-adamantan-1-yl-N-(3,4-dihydroxybenzyl)-2,4-dihydroxy-benzoic acid amide, 5-adamantan-1-yl-N-(3,4-dihydroxybenzyl)-2-hydroxy-4-methoxy-benzoic acid amide, 5-adamantan-1-yl-2,4-dihydroxy-N-[2-(4-hydroxyphenyl)-ethyl]-benzoic acid amide, 5-adamantan-1-yl-2-hydroxy-N-[2-(4-hydroxyphenyl)-ethyl]-4-methoxy-benzoic acid amide, 5-adamantan-1-yl-N-[2-(4-hydroxyphenyl)-ethyl]-2,4-dimethoxy-benzoic acid amide, 5-adamantan-1-yl-N-(2,4-dihydroxybenzyl)-2,4-dihydroxy-benzoic acid amide, 5-adamantan-1-yl-N-(2,4-dihydroxybenzyl)-2-hydroxy-4-methoxy-benzoic acid amide, 5-adamantan-1-yl-N-(2,4-dihydroxybenzyl)-2,4-dimethoxy-benzoic acid amide, 3-adamantan-1-yl-N-(3,4-dihydroxybenzyl)-4-hydroxy-benzoic acid amide, 3-adamantan-1-yl-N-(3,4-dihydroxybenzyl)-4-methoxy-benzoic acid amide, 3-adamantan-1-yl-N-[2-(3,4-dihydroxyphenyl)-ethyl]-4-hydroxy-benzoic acid amide, 3-adamantan-1-yl-N-[2-(3,4-dihydroxyphenyl)-ethyl]-4-methoxy-benzoic acid amide, 3-adamantan-1-yl-4-hydroxy-N-[2-(4-hydroxyphenyl)-ethyl]-benzoic acid amide, 3-adamantan-1-yl-N-[2-(4-hydroxyphenyl)-ethyl]-4-methoxy-benzoic acid amide, 3-adamantan-1-yl-N-(2,4-dihydroxybenzyl)-4-hydroxy-benzoic acid amide, 3-adamantan-1-yl-N-(2,4-dihydroxybenzyl)-4-methoxy-benzoic acid amide,
5-adamantan-1-yl-N-(2,5-dimethoxybenzyl)-2,4-dihydroxy-benzoic acid amide,
5-adamantan-1-yl-N-(2,5-dihydroxybenzyl)-2,4-dihydroxy-benzoic acid amide,
5-adamantan-1-yl-N-(3,5-dimethoxybenzyl)-2,4-dihydroxy-benzoic acid amide and
5-adamantan-1-yl-2,4-dihydroxy-N-(3-hydroxy-5-methoxybenzyl)-benzoic acid amide, an isomer thereof, a pharmaceutically acceptable salt thereof, a hydrate thereof or a solvate thereof.

In one aspect of the present invention, the solute may be 5-adamantan-1-yl-N-(2,4-dihydroxybenzyl)-2,4-dimethoxy-benzoic acid amide.

In one aspect of the present invention, the composition may comprise a water-soluble polar solvent as a solvent. Specifically, the composition may use water as a solvent.

In one aspect of the present invention, the cyclodextrin may be at least one of α-cyclodextrin, β-cyclodextrin, γ-cyclodextrin, hydroxypropyl-α-cyclodextrin, hydroxypropyl-β-cyclodextrin and hydroxypropyl-γ-cyclodextrin.

In one aspect of the present invention, the weight ratio of the solute and the first solubilizer may be 1:0.1 to 100. Specifically, the weight ratio of the solute and the first solubilizer may be 1:0.3 or more, 1:0.5 or more, 1:0.6 or more, 1:0.8 or more, 1:1 or more, 1:1.5 or more, 1:2.0 or more, 1:2.5 or more, 1:3.0 or more, 1:3.5 or more, 1:4.0 or more, 1:4.5 or more, 1:5 or more, 1:6 or more, 1:7 or more, 1:8 or more, 1:9 or more, 1:10 or more, 1:11 or more, 1:12 or more, 1:13 or more, 1:14 or more, 1:15 or more, 1:16 or more, 1:17 or more, or 1:19 or more. In addition, the weight ratio of the solute and the first solubilizer may be 1:100 or less, 1:90 or less, 1:85 or less, 1:80 or less, 1:75 or less, 1:70 or less, 1:65 or less, 1:60 or less, 1:50 or less, 1:40 or less, 1:30 or less, 1:25 or less, 1:24 or less, 1:23 or less, 1:22 or less, 1:21 or less, or 1:20.5 or less. Specifically, the weight ratio of the solute and the first solubilizer may be 1:0.5 to 25.

In one aspect of the present invention, the first solubilizer may be hydroxypropyl-β-cyclodextrin, and the weight ratio of the solute and the first solubilizer may be of 1:2 to 100. Specifically, when the first solubilizer is hydroxypropyl-β-cyclodextrin, the weight ratio of the solute and the first solubilizer may be 1:2 or more, 1:3 or more, 1:4 or more, 1:5 or more, 1:6 or more, 1:7 or more, 1:8 or more, 1:9 or more, 1:10 or more, 1:11 or more, 1:12 or more, 1:13 or more, 1:14 or more, 1:15 or more, 1:16 or more, 1:17 or more or 1:19 or more. In addition, the weight ratio may be 1:100 or less, 1:90 or less, 1:85 or less, 1:80 or less, 1:75 or less, 1:70 or less, 1:65 or less, 1:60 or less, 1:50 or less, 1:40 or less, 1:30 or less, 1:25 or less, 1:24 or less, 1:23 or less, 1:22 or less, 1:21 or less, or 1:20.5 or less.

In one aspect of the present invention, the first solubilizer may comprise hydroxypropyl-β-cyclodextrin and γ-cyclodextrin at a weight ratio of 1:0.1 to 10, and the weight ratio of the solute and the first solubilizer may be 1:0.1 to 100. Specifically, the first solubilizer may be a mixture of hydroxypropyl-β-cyclodextrin and γ-cyclodextrin, and the weight ratio thereof may be 1:0.1 or more, 1:0.3 or more, 1:0.5 or more, 1:0.6 or more, 1:0.8 or more, or 1:1 or more. In addition, the weight ratio thereof may be 1:10 or less, 1:9 or less, 1:8 or less, 1:7 or less, 1:6 or less, 1:5 or less, 1:4 or less, 1:3 or less, or 1:2 or less.

When the first solubilizer is a mixture of hydroxypropyl-β-cyclodextrin and γ-cyclodextrin, the weight ratio of the solute and the first solubilizer may be 1:0.1 to 100. Specifically, the weight ratio of the solute and the first solubilizer may be 1:0.3 or more, 1:0.5 or more, 1:0.6 or more, 1:0.8 or more, 1:1 or more, 1:1.5 or more, 1:2.0 or more, 1:2.5 or more, 1:3.0 or more, 1:3.5 or more, 1:4.0 or more, 1:4.5 or more, 1:5 or more, 1:6 or more, 1:7 or more, 1:8 or more, 1:9 or more, 1:10 or more, 1:11 or more, 1:12 or more, 1:13 or more, 1:14 or more, 1:15 or more, 1:16 or more, 1:17 or more, or 1:19 or more. In addition, the weight ratio of the solute and the first solubilizer may be 1:100 or less, 1:90 or less, 1:85 or less, 1:80 or less, 1:75 or less, 1:70 or less, 1:65 or less, 1:60 or less, 1:50 or less, 1:40 or less, 1:30 or less, 1:25 or less, 1:24 or less, 1:23 or less, 1:22 or less, 1:21 or less, or 1:20.5 or less. Preferably, the weight ratio of the solute and the first solubilizer may be 1:0.5 to 25.

Another aspect of the present invention provides a composition for external application to the skin further comprising a pH adjuster. In another aspect of the present invention, when the composition comprising the compound of Formula 1 further comprises a pH adjuster in addition to cyclodextrin to improve the solubility of the composition, the solubility of the composition can be improved even with a small amount of cyclodextrin.

As used herein, the term "pH adjuster" refers to an acidic or basic material for controlling the pH of a composition. In one embodiment, the pH adjuster of the present invention may preferably be a basic compound.

In another aspect of the present invention, the pH adjuster may be at least one of potassium hydroxide (KOH), calcium hydroxide ($Ca(OH)_2$), sodium carbonate ($Na_2CO_3$), potassium carbonate ($K_2CO_3$), sodium bicarbonate ($NaHCO_3$), lithium hydroxide (LiOH), citric acid, lactic acid, 2-aminobutanol, acetic acid, acetyl mandelic acid, adipic acid, aluminum hydroxide oxide, aluminum triformate, aminoethyl propanediol, aminomethyl propanediol, aminomethyl propanol, aminopropanediol, ammonia, ammonium bicarbonate, ammonium carbamate, ammonium carbonate, ammonium glycolate, ammonium hydroxide, ammonium phosphate, ascorbic acid, azelaic acid, babassu acid, benzylic acid, benzoic acid, bis-hydroxyethyl tromethamine, butyl diethanolamine, butylethanolamine, calcium citrate, calcium dihydrogen phosphate, calcium glycinate, calcium oxide, camphor sulfonic acid, chloroacetic acid, copper glycinate, dibutyl ethanolamine, diethanolamine, diethanolamine bisulfate, diisopropanolamine, diisopropylamine, dimethyl isopropanolamine, dimethyl MEA, dioleoyl edetolmonium methosulfate, dioleyl phosphate, dipotassium phosphate, dipropylenetriamine, disodium fumarate, disodium phosphate, disodium pyrophosphate, disodium tartrate, ethanolamine, ethanolamine HCl, ethyl ethanolamine, formic acid, fumaric acid, galacturonic acid, geranic acid, glucoheptonic acid, glucosamine HCl, glucuronic acid, glutaric acid, glycolic acid, glyoxylic acid, guanidine carbonate, hydrobromic acid, hydrochloric acid, imidazole, isopropanolamine, isopropylamine, ketoglutaric acid, lactobionic acid, lithium carbonate, magnesium carbonate, magnesium carbonate hydroxide, magnesium glycinate, magnesium hydroxide, magnesium oxide, maleic acid, malic acid, malonic acid, maltobionic acid, metaphosphoric acid, methoxy PEG-100/polyepsilon caprolactone ethylhexanoate, methoxy PEG-100/polyepsilon caprolactone palmitate, methoxy PEG-114/polyepsilon caprolactone, methylethanolamine, methylglucamine, morpholine, morpholinopropane sulfonic acid, oxalic acid, p-anisic acid, pentapotassium triphosphate, pentasodium triphosphate, phenolsulfonphthalein, phosphoric acid, potassium bicarbonate, potassium biphthalate, potassium borate, potassium citrate, potassium magnesium aspartate, potassium oxide, potassium phosphate, potassium tartrate, propionic acid, quinic acid, ribonic acid, sebacic acid, sesquiethoxytriethanolamine, sodium aluminate, sodium anisate, sodium arachidate, sodium bisulfate, sodium borate, sodium calcium boron phosphate, sodium calcium copper phosphate, sodium calcium zinc phosphate, sodium cinnamate, sodium citrate, sodium cyanate, sodium fumarate, sodium glycolate, sodium hydroxide, sodium oxide, sodium sesquicarbonate, sodium silicate, sodium succinate, sodium trimetaphosphate, sodium tungstate antimonate, strontium hydroxide, succinic acid, sulfonated styrene/DVB crosspolymer, sulfuric acid, tartaric acid, TEA-diricinoleate/IPDI copolymer, tetrapotassium pyrophosphate, tetrasodium pyrophosphate, triethanolamine, triisopropanolamine, trisodium phosphate, trisodium sulfosuccinate, tromethamine, vinegar, zinc carbonate hydroxide, zinc glycinate, and zinc magnesium aspartate.

In another aspect of the present invention, when the composition for external application to the skin has a pH of 2 or higher, the weight ratio of the solute and the first solubilizer may be 1:0.1 to 50.

Specifically, the pH may be 2 or higher, 2.3 or higher, 2.5 or higher, 2.8 or higher, 3.0 or higher, 3.2 or higher, 3.5 or higher, 3.8 or higher, 4.0 or higher, 4.3 or higher, 4.8 or higher, 5.0 or higher, 5.3 or higher, 5.8 or higher, 6.0 or higher, 6.3 or higher, 6.8 or higher, 7.0 or higher, 7.3 or higher, 7.8 or higher, 8.0 or higher, 8.3 or higher, 8.8 or higher, 9.0 or higher, 9.3 or higher, 9.4 or higher, 9.5 or higher, 9.6 or higher, 9.7 or higher, 9.8 or higher, 9.9 or higher, 10.0 or higher, 10.1 or higher, 10.2 or higher, 10.3 or higher, or 10.4 or higher. In addition, when the composition for external application to the skin has a pH of 2 or higher, the weight ratio of the solute and the first solubilizer may be 1:0.1 or higher, 1:0.2 or higher, 1:0.3 or higher, 1:0.5 or higher, 1:0.6 or higher, 1:0.8 or higher, 1:1 or higher, 1:1.5 or higher, 1:2.0 or higher, 1:2.5 or higher, 1:3.0 or higher, 1:3.5 or higher, 1:4.0 or higher, 1:4.5 or higher, 1:5 or higher, 1:6 or higher, 1:7 or higher, 1:8 or higher, 1:9 or higher, 1:10 or higher, 1:11 or higher, 1:12 or higher, 1:13 or higher, 1:14 or higher, 1:15 or higher, 1:16 or higher, 1:17 or higher, or 1:19 or higher. In addition, the weight ratio may be 1:50 or lower, 1:40 or lower, 1:30 or lower, 1:25 or lower, 1:24 or lower, 1:23 or lower, 1:22 or lower, 1:21 or lower, 1:20.5 or lower, 1:20 or lower, 1:19 or lower, 1:18 or lower, 1:17 or lower, 1:15 or lower, 1:13 or lower, 1:12 or lower, 1:11 or lower, 1:10 or lower, 1:8 or lower, 1:7 or lower, 1:6 or lower, 1:5 or lower, 1:4 or lower, or 1:3 or lower.

In another aspect of the present invention, when the composition for external application to the skin has a pH of 2 to 10, the weight ratio of the solute and the first solubilizer may be 1:4 to 12, and the first solubilizer may be hydroxypropyl-β-cyclodextrin.

Specifically, the pH may be 2 or higher, 2.3 or higher, 2.5 or higher, 2.8 or higher, 3.0 or higher, 3.2 or higher, 3.5 or higher, 3.8 or higher, 4.0 or higher, 4.3 or higher, 4.8 or higher, 5.0 or higher, 5.3 or higher, 5.8 or higher, 6.0 or higher, 6.3 or higher, 6.8 or higher, 7.0 or higher, 7.3 or higher, 7.8 or higher, 8.0 or higher, 8.3 or higher, 8.8 or higher, or 9.0 or higher. In addition, the pH may be 10 or lower, 9.5 or lower, 9.2 or lower, 9.0 or lower, 8.8 or lower, 8.5 or lower, 8.0 or lower, 7.5 or lower, 7.0 or lower, 6.5 or lower, 6.0 or lower, 5.5 or lower, or 5.0 or lower. In addition, when the composition for external application to the skin has a pH of 2 to 10, the weight ratio of the solute and the first solubilizer may be 1:4 or higher, 1:5 or higher, 1:6 or higher, 1:7 or higher, 1:8 or higher, 1:9 or higher, or 1:10 or higher. In addition, the weight ratio may be 1:12 or lower, 1:11 or lower, 1:10 or lower, 1:9 or lower, 1:8 or lower, 1:7 or lower, 1:6 or lower, 1:5 or lower or 1:4 or lower.

In one or more aspects of the present invention, the content of the solute may be 0.01 to 20% by weight based on the total weight of the composition.

In one aspect of the present invention, the content of the solute may be 0.01 to 20% by weight based on the total weight of the composition. The content of the solute of the present invention may be 0.01 to 20% by weight, specifically 0.1 to 10% by weight, more specifically 0.5 to 5% by weight, based on the total weight of the composition. When the content is within the above range, it is not only suitable for achieving the desired effect of the present invention but also can satisfy both the stability and safety of the composition. Further, it would also be suitable in terms of cost effectiveness. Specifically, when the content is less than 0.01% by weight, it cannot obtain a sufficient skin whitening effect, and when the content exceeds 20% by weight, it is not cost-effective and thus may not be preferable.

In one or more aspects of the present invention, the composition may further comprise a second solubilizer which is at least one selected from the group consisting of xanthan gum, hydroxypropyl methylcellulose, sodium polyacrylate, sodium magnesium silicate, hydroxyethyl acrylate/sodium acryloyldimethyl taurate copolymer, polyacrylate-13/polyisobutene/polysorbate-20, PEG-240/HDI copolymer bis-decyltetraceth-20 ether and magnesium aluminum silicate.

In one or more aspects of the present invention, the composition may further comprise a third solubilizer which is at least one of diethylene glycol monoethyl ether, methyl gluceth, glyceryl ether, polyethylene glycol, and polyethylene glycol/polypropylene glycol copolymer.

In one or more aspects of the present invention, the methyl gluceth may be methyl gluceth 10 or methyl gluceth 20, the glyceryl ether may be glycereth-26 or glycereth-12, the polyethylene glycol may be PEG-8 or PEG-6, and the polyethylene glycol/polypropylene glycol copolymer may be PEG/PPG-17/6 copolymer.

In another aspect of the present invention, the composition for external application to the skin may be a composition for skin whitening. The composition for external application to the skin can exhibit an excellent skin whitening effect. Specifically, it can improve or prevent melasma, freckles, nevus and skin pigmentation.

In another aspect of the present invention, the composition for external application to the skin may be a pharmaceutical or cosmetic composition.

In one aspect of the present invention, the composition may be a cosmetic composition. The cosmetic composition of the present invention may be prepared into any formulation conventionally used in the art, such as a solution, a suspension, an emulsion, a paste, a gel, a cream, a lotion, a powder, a soap, a surfactant-containing cleanser, an oil, a powder foundation, an emulsion foundation, a wax foundation, and a spray, although not limited thereto.

In one aspect of the present invention, the composition may be a pharmaceutical composition. The pharmaceutical composition can exhibit an excellent skin whitening effect. Specifically, it can improve or prevent melasma, freckles, nevus and skin pigmentation. The pharmaceutical composition according to one aspect of the present invention may be administered parenterally, rectally, topically, transdermally, intravenously, intramuscularly, intraperitoneally, subcutaneously, etc. Formulations for parenteral administration include, but are not limited to, solutions, suspensions, emulsions, gels, injections, drops, suppositories, patches and aerosols. The formulations may be readily prepared according to conventional methods in the art and may further comprise a surfactant, an excipient, a hydrant, an emulsification promoter, a suspending agent, a salt or buffer for osmotic pressure control, a colorant, a fragrance, a stabilizer, a preservative, an antiseptic or other commonly used adjuvants, as appropriate.

The dose of the active ingredient of the pharmaceutical composition according to one aspect of the present invention will vary depending on the age, gender, body weight, pathological condition and severity of the subject, route of administration, and judgment of the prescriber. The determination of the dose based on these factors is within the knowledge of those skilled in the art. The daily dose of the active ingredient may be 0.1 mg/kg/day to 100 mg/kg/day, specifically 5 mg/kg/day to 50 mg/kg/day, although not limited thereto.

In another aspect, the present invention provides a method for preventing, ameliorating, or treating diseases associated with skin whitening, such as melasma, freckles, nevus, and skin pigmentation, comprising administering to a subject in need of prevention, amelioration, or treatment of diseases associated with skin whitening, such as melasma, freckles, nevus, and skin pigmentation, a composition comprising a solute which is a compound represented by Formula 1, an isomer thereof, a pharmaceutically acceptable salt thereof, a hydrate thereof or a solvate thereof; and a first solubilizer which is cyclodextrin. In one aspect of the present invention, the administration of the method may be carried out according to an administration method and administration dose described herein.

In another aspect, the present invention may relate to the use of a solute which is a compound represented by Formula 1, an isomer thereof, a pharmaceutically acceptable salt thereof, a hydrate thereof or a solvate thereof; and a first solubilizer which is cyclodextrin for preparation of a pharmaceutical composition for skin whitening.

In another aspect, the present invention may relate to the use of a solute which is a compound represented by Formula 1, an isomer thereof, a pharmaceutically acceptable salt thereof, a hydrate thereof or a solvate thereof; and a first solubilizer which is cyclodextrin for preparation of a cosmetic composition for skin whitening.

In another aspect, the present invention may relate to the use of a composition comprising a solute which is a compound represented by Formula 1, an isomer thereof, a pharmaceutically acceptable salt thereof, a hydrate thereof or a solvate thereof; and a first solubilizer which is cyclodextrin for skin whitening.

In another aspect, the present invention may relate to a composition for skin whitening comprising a solute which is a compound represented by Formula 1, an isomer thereof, a pharmaceutically acceptable salt thereof, a hydrate thereof or a solvate thereof; and a first solubilizer which is cyclodextrin.

EXAMPLES

Hereinafter, the present invention will be described in more detail with reference to examples. It will be apparent to those skilled in the art that these examples are for illustrative purposes only, and the scope of the present invention is not construed as being limited by these examples.

Test Example 1: Solubility of Cyclodextrin in 5-adamantan-1-yl-N-(2,4-dihydroxybenzyl)-2,4-dimethoxy-benzoic acid amide HP-β-CD (Nihon Shokunin Kako, Japan) and 5-adamantan-1-yl-N-(2,4-dihydroxybenzyl)-2,4-dimethoxy-benzoic acid amide (hereinafter "DBAB") were mixed at various weight ratios as shown in Table 1 below and then mixed while heating up to 50° C. After mixing with heating for at least 10 minutes, the mixture was stored at a room temperature of 25° C. to 30° C. for 7 days, and then the presence or absence of precipitation was determined. In particular, in Example 1-6, the composition of Example 1-5 with the weight ratio of 20:1 was diluted with water and then the presence or absence of precipitation was determined.

TABLE 1

|  | Example 1-1 | Example 1-2 | Example 1-3 | Example 1-4 | Example 1-5 | Example 1-6 |
|---|---|---|---|---|---|---|
| HP-β-CD:DBAB | 5:1 | 10:1 | 15:1 | 17:1 | 20:1 | Example 1-5 was diluted with water and the presence or absence of precipitation was determined |

Figure 1:
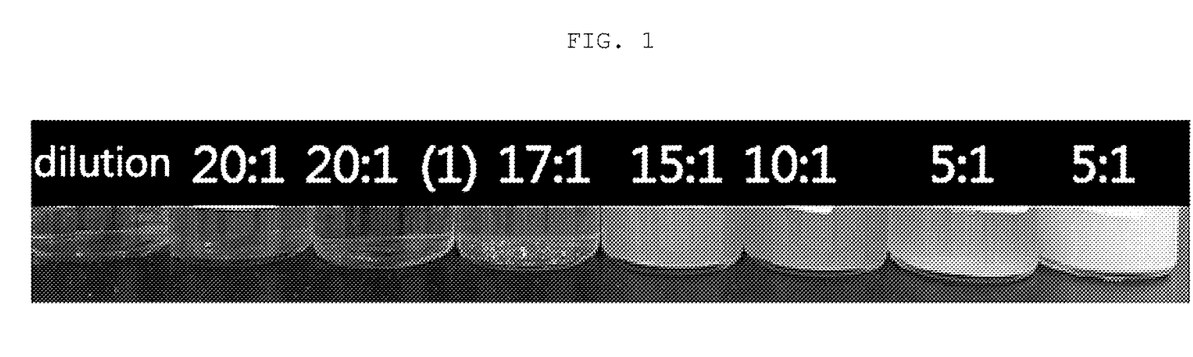
FIG. 1 is a photograph showing the solubility with varying the weight ratio of DBAB and HP-β-CD according to Test Example 1 of the present invention.

The test results are shown in FIG. 1. As can be seen in FIG. 1, the composition was transparently dissolved when the weight ratio of HP-β-CD and DBAB was 20 or more:1.

Test Example 2: Investigation of the Synergistic Effect of Cyclodextrin in Combination with Other Solubilizers The synergistic effect of cyclodextrin as a solubilizer of the present invention in combination with other solubilizers (a second solubilizer and a third solubilizer) was investigated.

Comparative Example 2-1: When PEG.PPG-17.6 copolymer as a second solubilizer was solely used for dissolving 0.1 g of DBAB in water, 50 g of PEG.PPG-17.6 copolymer was needed.

Example 2-1: When 0.6 g of HP-β-CD was used for dissolving 0.1 g of DBAB in water, 30 g of PEG.PPG-17.6 copolymer as a second solubilizer was needed.

The results of Comparative Example 2-1 and Example 2-1 show that, in a composition comprising DBAB, 0.6% of HP-β-CD replaces 20% of PEG.PPG-17.6 copolymer.

Comparative Example 2-2: At least 45 g of PEG.PPG-17.6 copolymer as a second solubilizer and 0.5 g of HPMC as a third solubilizer were needed to dissolve 0.1 g of DBAB in water.

Comparative Example 2-3: 30 g of PEG.PPG-17.6 copolymer as a second solubilizer and 2 g of HPMC were needed to dissolve 0.1 g of DBAB in water.

Example 2-2: When 0.6 g of HP-β-CD was used for dissolving 0.1 g of DBAB in water, 5 g of PEG.PPG-17.6 copolymer as a second solubilizer and 0.5 g of hydroxylpropyl methyl cellulose (HPMC) as a third solubilizer were needed.

The results of Comparative Examples 2-2 and 2-3 and Example 2-2 show that, in a composition comprising DBAB, HP-β-CD replaces PEG.PPG-17.6 copolymer as a second solubilizer and HPMC as a third solubilizer.

Test Example 3: Investigation of pH and Solubility of Cyclodextrin

In Comparative Example 3-1, HP-β-CD and DBAB were mixed at a weight ratio of 1:1 and then purified water was added at a ratio of 20. The resultant composition was found to be opaque. The composition had a pH of 7.76.

The solubility of the composition of Comparative Example 3-1 was investigated with varying the pH of the composition as shown in Table 2 below by adding KOH or lactic acid as a pH adjuster.

of their 1:1 weight ratio combinations was determined, as shown in Table 4 below. From Test Example 1 and FIG. 1, DBAB was found to be transparently dissolved at the weight ratio of CD and DBAB of 20:1. From the corresponding combination in Table 4 below, the amount of CD required was verified.

TABLE 4

|     | α   | β   | γ   | HPα | HPβ | HPγ |
| --- | --- | --- | --- | --- | --- | --- |
| α   | >20 | >20 | >20 | >20 | >20 | >20 |
| β   |     | >20 | >20 | >20 | >20 | >20 |
| γ   |     |     | >20 | >20 | <20 | >20 |
| HPα |     |     |     | >20 | >20 | >20 |

TABLE 2

|                        | Comparative Example 3-2 | Comparative Example 3-3 | Comparative Example 3-4 | Comparative Example 3-5 | Comparative Example 3-6 | Comparative Example 3-7 | Comparative Example 3-8 | Comparative Example 3-9 | Comparative Example 3-10 |
| --- | --- | --- | --- | --- | --- | --- | --- | --- | --- |
| pH | 4.08 | 4.26 | 4.5 | 4.81 | 5.66 | 6.44 | 6.72 | 7.39 | 8.18 |
| Whether it is soluble | Opaque | Opaque | Opaque | Opaque | Opaque | Opaque | Opaque | Opaque | Opaque |

|                        | Comparative Example 3-11 | Comparative Example 3-12 | Comparative Example 3-13 | Comparative Example 3-14 | Comparative Example 3-15 | Comparative Example 3-16 | Comparative Example 3-17 | Example 3-1 | Example 3-2 |
| --- | --- | --- | --- | --- | --- | --- | --- | --- | --- |
| pH | 8.71 | 8.87 | 8.92 | 9.07 | 9.16 | 9.22 | 9.47 | 12.72 | 13.01 |
| Whether it is soluble | Opaque | Opaque | Opaque | Opaque | Opaque | Opaque | Opaque | Transparent | Transparent |

The result shows that the composition in which HP-β-CD and DBAB are mixed at a weight ratio of 1:1 has improved solubility at a pH of 12.72 or higher.

In addition to investigation of the solubility improvement with varying pH, the solubility of the composition was investigated with varying the pH of the composition and the weight ratio of HP-β-CD and DBAB as shown in Table 3 below.

TABLE 4-continued

|     | α   | β   | γ   | HPα | HPβ | HPγ |
| --- | --- | --- | --- | --- | --- | --- |
| HPβ |     |     |     |     | 20  | >20 |
| HPγ |     |     |     |     |     | >20 |

TABLE 3

|                           | Example 3-3 | Example 3-4 | Example 3-5 | Example 3-6 | Example 3-7 | Example 3-8 | Example 3-9 | Example 3-10 |
| --- | --- | --- | --- | --- | --- | --- | --- | --- |
| Weight ratio of HP-β-CD:DBAB | 10:1 | 8:1 | 7:1 | 6:1 | 5:1 | 4:1 | 3:1 | 2:1 |
| pH | 3.01 | 3.77 | 4.12 | 8.23 | 9.51 | 10.82 | 11.06 | 10.74 |
| Whether it is soluble | Transparent | Transparent | Transparent | Transparent | Transparent | Transparent | Transparent | Transparent |

Figure 2:
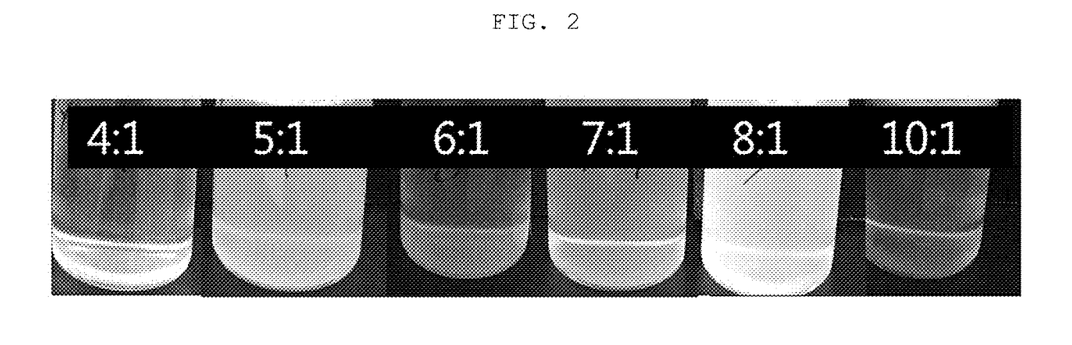
FIG. 2 is a photograph of the composition of Table 3 of Test Example 3 of the present invention.

The photographs of Examples 3-3 to 3-8 indicated in Table 3 are shown in FIG. 2.

As can be seen from Table 3, the higher the CD ratio, the lower the pH at which the composition was transparently dissolved. However, when the ratio was 4 or less:1 (3:1, 2:1, etc.), the effect was reduced to some extent.

Test Example 4: Investigation of Solubility of Each Type of Cyclodextrin and Synergistic Effect Between Cyclodextrins In order to investigate the solubility of one part by weight of DBAB for each type of cyclodextrin and the synergistic effect between cyclodextrins, the solubility of each of α-CD, γ-CD, HP-α-CD, HP-β-CD and HP-γ-CD and the solubility Table 4 shows that the solubility of DBAB is higher at the weight ratio of HP-β-CD and γ-CD of 1:1 than other cyclodextrin mixtures. As shown in Table 4, under the same conditions, the solubility was improved when HP-β-CD was solely used and when HP-β-CD and γ-CD were mixed at a ratio of 1:1.

In addition to the above results, the solubility of DBAB was investigated at various weight ratios of HP-β-CD and γ-CD such that the total weight of CD was 0.5%, as shown in Table 5 below. In this case, 10% by weight of PEG.PPG-17.6 copolymer, 0.1% by weight of DBAB, 39.4% by weight of propanediol, 50% by weight of water and 0.5% by weight of the total CD were used. Among the total CD content, no combination other than the 1:1 combination showed a solubility improvement effect, as shown in Table 5 below.

When 50% by weight of PEG.PPG-17.6 copolymer, 0.1% by weight of DBAB, and the balance of water were used, the composition was transparently dissolved. When HP-β-CD was solely used, the composition was transparently dissolved only when 30% by weight of PEG.PPG-17.6 copolymer, 0.1% by weight of DBAB, and 0.6% by weight of HP-β-CD were used. 0.1% by weight of HP-β-CD has an effect of replacing 20% by weight of PEG.PPG-17.6 copolymer. Also, the solubility of DBAB achieved by propanediol is 5.92 mg/mL, which is very low compared to the solubility achieved by PEG.PPG-17.6 copolymer, 81.26 mg/mL.

Therefore, it can be expected that when a 1:1 mixture of HP-β-CD and γ-CD is used, the conventional content of 0.6% by weight can be reduced to 0.4% by weight.

TABLE 5

| HPβ/γ | 0.4% | 0.3% | 0.25% | 0.2% | 0.1% |
|---|---|---|---|---|---|
| 0.1% | Insoluble | | | | |
| 0.2% | | Insoluble | | | |
| 0.25% | | | Transparently dissolved | | |
| 0.3% | | | | Insoluble | |
| 0.4% | | | | | Insoluble |

In addition, the test method of Table 5 was carried out by using 0.2% by weight of each of HP-β-CD and γ-CD with an addition of 0.1% by weight of HP-α-CD, HP-γ-CD, α-CD or β-CD. According to the results, none of the four types did not improve the solubility.

Test Example 5: Investigation of the Effect of Stabilization in Formulations

Caprylic/capric triglyceride, Coco-Glucoside And Coconut Alcohol, glyceryl oleate, dextrin myristate, and disteardimonium hectorite were weighed together in a beaker according to the composition of Table 6 below and heated to a temperature of 70° C. The other ingredients were weighed in another beaker and mixed with a homomixer (homomixer Mark 2, Primix, Japan) at 3000 rpm for 5 minutes, followed by cooling. At around 50° C., cyclopentasiloxane was mixed with a homomixer at 3000 rpm for 5 minutes and cooled to 30° C. to prepare a formulation.

Figure 3:
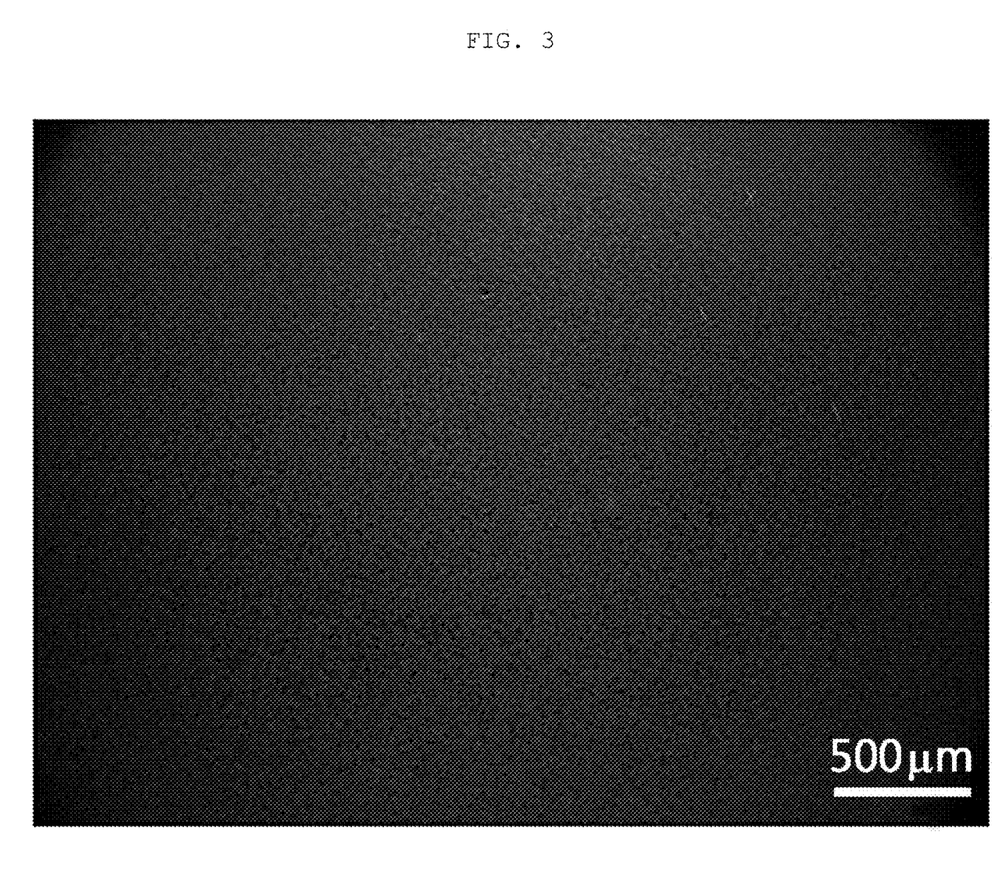
FIG. 3 is a polarizing microscope photograph of Example 4 of Test Example 5 of the present invention.

It was investigated whether DBAB precipitated from the formulations of Comparative Example 4 and Example 4, by using a polarizing microscope. The 1/10 dilution in water of Example 4 exhibited a pH of 7.68. When stored in a thermostatic bath at 45° C. for 1 month after preparation, Comparative Example 4 showed precipitation whereas Example 4 did not exhibit precipitation (FIG. 3).

TABLE 6

| | Comparative Example 4 | Example 4 |
|---|---|---|
| DBAB | 0.1% by weight | 0.1% by weight |
| NaOH 10% solution | — | 0.5% by weight |
| HP-β-CD | — | 1.0% by weight |
| Caprylic/capric triglyceride | 4.5% by weight | 4.5% by weight |
| Coco-Glucoside And Coconut Alcohol | 1.6% by weight | 1.6% by weight |
| Glyceryl oleate | 0.4% by weight | 0.4% by weight |
| Dextrin myristate | 0.2% by weight | 0.2% by weight |
| Disteardimonium hectorite | 0.5% by weight | 0.5% by weight |
| Cyclopentasiloxane | 4.5% by weight | 4.5% by weight |
| 1,2-hexanediol | 0.7% by weight | 0.7% by weight |

TABLE 6-continued

| | Comparative Example 4 | Example 4 |
|---|---|---|
| Ethylhexyl glycerin | 0.05% by weight | 0.05% by weight |
| Sodium hyaluronate | 0.05% by weight | 0.05% by weight |
| Cellulose gum | 0.7% by weight | 0.7% by weight |
| Hydroxyethyl acrylate/sodium acryloyldimethyltaurate copolymer | 0.1% by weight | 0.1% by weight |
| Purified water | Balance | Balance |

Test Example 6: Measurement of Feeling of Use of Comparative Example 4 and Example 4

The feeling of use was measured for Comparative Example 4 and Example 4. The moisturizing feeling, stickiness, and softness after use were subjectively scored on a 9-point scale by the evaluator. According to the results, in Example 4, stickiness decreased from about 5.9 to about 4 and the moisturizing feeling increased from about 4 to about 6, compared to Comparative Example 4.

Hereinafter, formulation examples according to the present invention will be described. However, these examples are for illustrative purposes only and are not intended to limit the scope of the present invention.

[Formulation Example 1] Softening Lotion

Softening lotion was prepared according to a conventional method with the composition shown in Table 7 below.

TABLE 7

| Ingredient | Content (% by weight) |
|---|---|
| DBAB | 0.1% by weight |
| KOH | 0.06% by weight |
| HP-β-CD | 1.0% by weight |
| PEG-30 hydrogenated castor oil | 1.2% by weight |
| Ethanol | 5.0% by weight |
| Butylene glycol | 2.0% by weight |
| Propylene glycol | 2.0% by weight |
| Preservative, colorant, fragrance | q.s. |
| Purified water | Balance |

[Formulation Example 2] Nourishing Lotion (Milk Lotion)

Nourishing lotion was prepared according to a conventional method with the composition shown in Table 8 below.

TABLE 8

| Ingredient | Content (% by weight) |
|---|---|
| DBAB | 0.1% by weight |
| KOH | 0.06% by weight |
| HP-β-CD | 1.0% by weight |
| PEG-30 hydrogenated castor oil | 2.0% by weight |
| Glycerin | 3.0% by weight |
| Butylene glycol | 3.0% by weight |
| Propylene glycol | 3.0% by weight |
| Carboxyvinyl polymer | 0.1% by weight |
| Wax | 4.0% by weight |
| Caprylic/capric triglyceride | 5.0% by weight |
| Squalane | 5.0% by weight |
| Liquid paraffin | 0.5% by weight |
| Cetearyl alcohol | 1.0% by weight |
| Triethanolamine | 0.2% by weight |

[Formulation Example 3] Nourishing Cream

Nourishing cream was prepared according to a conventional method with the composition shown in Table 9 below.

TABLE 9

| Ingredient | Content (% by weight) |
| --- | --- |
| DBAB | 0.1% by weight |
| KOH | 0.06% by weight |
| HP-β-CD | 1.0% by weight |
| PEG-30 hydrogenated castor oil | 3.0% by weight |
| Glycerin | 3.0% by weight |
| Butylene glycol | 3.0% by weight |
| Liquid paraffin | 7.0% by weight |
| Beta-glucan | 7.0% by weight |
| Carbomer | 0.1% by weight |
| Caprylic/capric triglyceride | 3.0% by weight |
| Squalane | 5.0% by weight |
| Cetearyl glucoside | 1.5% by weight |
| Sorbitan stearate | 0.4% by weight |
| Triethanolamine | 0.1% by weight |
| Preservative, colorant, fragrance | q.s. |
| Purified water | Balance |

[Formulation Example 4] Massage Cream

Massage cream was prepared according to a conventional method with the composition shown in Table 10 below.

TABLE 10

| Ingredient | Content (% by weight) |
| --- | --- |
| DBAB | 0.1% by weight |
| KOH | 0.06% by weight |
| HP-β-CD | 1.0% by weight |
| PEG-30 hydrogenated castor oil | 4.0% by weight |
| Vitamin E acetate | 5.0% by weight |
| Glycerin | 8.0% by weight |
| Butylene glycol | 4.0% by weight |
| Liquid paraffin | 45.0% by weight |
| Beta-glucan | 7.0% by weight |
| Carbomer | 0.1% by weight |
| Caprylic/capric triglyceride | 3.0% by weight |
| Wax | 4.0% by weight |
| Cetearyl glucoside | 1.5% by weight |
| Sorbitan sesquioleate | 0.9% by weight |
| Vaseline | 3.0% by weight |
| Paraffin | 1.5% by weight |
| Preservative, colorant, fragrance | q.s. |
| Purified water | Balance |

[Formulation Example 5] Pack

Pack was prepared according to a conventional method with the composition shown in Table 11 below.

TABLE 11

| Ingredient | Content (% by weight) |
| --- | --- |
| DBAB | 0.1% by weight |
| KOH | 0.06% by weight |
| HP-β-CD | 1.0% by weight |
| PEG-30 hydrogenated castor oil | 4.0% by weight |
| Vitamin E acetate | 8.0% by weight |
| Glycerin | 4.0% by weight |
| Polyvinyl alcohol | 15.0% by weight |
| Hyaluronic acid extract | 5.0% by weight |
| Beta-glucan | 7.0% by weight |
| Allantoin | 0.1% by weight |
| Nonyl phenyl ether | 0.4% by weight |
| Polysorbate 60 | 1.2% by weight |
| Ethanol | 6.0% by weight |
| Preservative, colorant, fragrance | q.s. |
| Purified water | Balance |

[Formulation Example 6] Ointment

Ointment was prepared according to a conventional method with the composition shown in Table 12 below.

TABLE 12

| Ingredient | Content (% by weight) |
| --- | --- |
| DBAB | 0.1% by weight |
| KOH | 0.06% by weight |
| HP-β-CD | 1.0% by weight |
| PEG-30 hydrogenated castor oil | 3.0% by weight |
| Vitamin E acetate | 4.0% by weight |
| Butylene glycol | 4.0% by weight |
| Liquid paraffin | 15.0% by weight |
| Beta-glucan | 7.0% by weight |
| Carbomer | 0.1% by weight |
| Caprylic/capric triglyceride | 3.0% by weight |
| Squalane | 1.0% by weight |
| Cetearyl glucoside | 1.5% by weight |
| Sorbitan stearate | 0.4% by weight |
| Cetearyl alcohol | 1.0% by weight |
| Wax | 4.0% by weight |

[Formulation Example 7] Hair Lotion

Hair lotion was prepared according to a conventional method with the composition shown in Table 13 below.

TABLE 13

| Ingredient | Content (% by weight) |
| --- | --- |
| DBAB | 0.1% by weight |
| KOH | 0.06% by weight |
| HP-β-CD | 1.0% by weight |
| PEG-30 hydrogenated castor oil | 3.0% by weight |
| Glycerin | 3.0% by weight |
| Butylene glycol | 3.0% by weight |
| Liquid paraffin | 7.0% by weight |
| Beta-glucan | 7.0% by weight |
| Carbomer | 0.1% by weight |
| Caprylic/capric triglyceride | 3.0% by weight |
| Squalane | 5.0% by weight |
| Cetearyl glucoside | 1.5% by weight |
| Sorbitan stearate | 0.4% by weight |
| Polysorbate | 1.2% by weight |
| Preservative, colorant, fragrance | q.s. |
| Triethanolamine | 0.1% by weight |
| Purified water | Balance |

TABLE 8-continued

| Ingredient | Content (% by weight) |
| --- | --- |
| Preservative, colorant, fragrance | q.s. |
| Purified water | Balance |

The invention claimed is:

1. A composition for external application to the skin comprising:
   a solute which is 5-adamantan-1-yl-N-(2,4-dihydroxybenzyl)-2,4-dimethoxy-benzoic acid amide, a pharmaceutically acceptable salt thereof, a hydrate thereof or a solvate thereof; and
   a first solubilizer which is cyclodextrin,
   wherein the cyclodextrin comprises hydroxypropyl-β-cyclodextrin and γ-cyclodextrin at a weight ratio of 1:0.1 to 10, and
   wherein the weight ratio of the solute to the first solubilizer is 1:1 to 20.

2. The composition for external application to the skin according to claim 1,
   wherein the weight ratio of the solute to the first solubilizer is 1:2 to 20.

3. The composition for external application to the skin according to claim 1,
   wherein the composition for external application to the skin further comprises a pH adjuster.

4. The composition for external application to the skin according to claim 3,
   wherein the pH adjuster is at least one of potassium hydroxide (KOH), calcium hydroxide (Ca(OH)$_2$), sodium carbonate (Na$_2$CO$_3$), potassium carbonate (K$_2$CO$_3$), sodium bicarbonate (NaHCO$_3$), lithium hydroxide (LiOH), citric acid, lactic acid, 2-aminobutanol, acetic acid, acetyl mandelic acid, adipic acid, aluminum hydroxide oxide, aluminum triformate, aminoethyl propanediol, aminomethyl propanediol, aminomethyl propanol, aminopropanediol, ammonia, ammonium bicarbonate, ammonium carbamate, ammonium carbonate, ammonium glycolate, ammonium hydroxide, ammonium phosphate, ascorbic acid, azelaic acid, babassu acid, benzylic acid, benzoic acid, bis-hydroxyethyl tromethamine, butyl diethanolamine, butylethanolamine, calcium citrate, calcium dihydrogen phosphate, calcium glycinate, calcium oxide, camphor sulfonic acid, chloroacetic acid, copper glycinate, dibutyl ethanolamine, diethanolamine, diethanolamine bisulfate, diisopropanolamine, diisopropylamine, dimethyl isopropanolamine, dimethyl MEA, dioleoyl edetolmonium methosulfate, dioleyl phosphate, dipotassium phosphate, dipropylenetriamine, disodium fumarate, disodium phosphate, disodium pyrophosphate, disodium tartrate, ethanolamine, ethanolamine HCl, ethyl ethanolamine, formic acid, fumaric acid, galacturonic acid, geranic acid, glucoheptonic acid, glucosamine HCl, glucuronic acid, glutaric acid, glycolic acid, glyoxylic acid, guanidine carbonate, hydrobromic acid, hydrochloric acid, imidazole, isopropanolamine, isopropylamine, ketoglutaric acid, lactobionic acid, lithium carbonate, magnesium carbonate, magnesium carbonate hydroxide, magnesium glycinate, magnesium hydroxide, magnesium oxide, maleic acid, malic acid, malonic acid, maltobionic acid, metaphosphoric acid, methoxy PEG-100/polyepsilon caprolactone ethylhexanoate, methoxy PEG-100/polyepsilon caprolactone palmitate, methoxy PEG-114/polyepsilon caprolactone, methylethanolamine, methylglucamine, morpholine, morpholinopropane sulfonic acid, oxalic acid, p-anisic acid, pentapotassium triphosphate, pentasodium triphosphate, phenolsulfonphthalein, phosphoric acid, potassium bicarbonate, potassium biphthalate, potassium borate, potassium citrate, potassium magnesium aspartate, potassium oxide, potassium phosphate, potassium tartrate, propionic acid, quinic acid, ribonic acid, sebacic acid, sesquiethoxytriethanolamine, sodium aluminate, sodium anisate, sodium arachidate, sodium bisulfate, sodium borate, sodium calcium boron phosphate, sodium calcium copper phosphate, sodium calcium zinc phosphate, sodium cinnamate, sodium citrate, sodium cyanate, sodium fumarate, sodium glycolate, sodium hydroxide, sodium oxide, sodium sesquicarbonate, sodium silicate, sodium succinate, sodium trimetaphosphate, sodium tungstate antimonate, strontium hydroxide, succinic acid, sulfonated styrene/DVB crosspolymer, sulfuric acid, tartaric acid, TEA-diricinoleate/IPDI copolymer, tetrapotassium pyrophosphate, tetrasodium pyrophosphate, triethanolamine, triisopropanolamine, trisodium phosphate, trisodium sulfosuccinate, tromethamine, vinegar, zinc carbonate hydroxide, zinc glycinate, or zinc magnesium aspartate.

5. The composition for external application to the skin according to claim 1,
   wherein, when the composition for external application to the skin has a pH of 2 or higher, the weight ratio of the solute to the first solubilizer is 1:1 to 20.

6. The composition for external application to the skin according to claim 5,
   wherein, when the composition for external application to the skin has a pH of 2 to 10, the weight ratio of the solute to the first solubilizer is 1:4 to 12.

7. The composition for external application to the skin according to claim 1,
   wherein the content of the solute is 0.01 to 20% by weight based on the total weight of the composition.

8. The composition for external application to the skin according to claim 1,
   wherein the composition comprises a second solubilizer which is at least one selected from the group consisting of xanthan gum, hydroxypropyl methylcellulose, sodium polyacrylate, sodium magnesium silicate, hydroxyethyl acrylate/sodium acryloyldimethyl taurate copolymer, polyacrylate-13/polyisobutene/polysorbate-20, PEG-240/HDI copolymer bis-decyltetraceth-20 ether and magnesium aluminum silicate.

9. The composition for external application to the skin according to claim 1,
   wherein the composition for external application to the skin is a pharmaceutical or cosmetic composition.

10. A method of skin whitening comprising administering a composition to a subject in need thereof, which the composition comprises:
    a solute which is 5-adamantan-1-yl-N-(2,4-dihydroxybenzyl)-2,4-dimethoxy-benzoic acid amide, a pharmaceutically acceptable salt thereof, a hydrate thereof or a solvate thereof; and
    a first solubilizer which is cyclodextrin:
    wherein the cyclodextrin comprises hydroxypropyl-β-cyclodextrin and γ-cyclodextrin at a weight ratio of 1:0.1 to 10, and
    wherein the weight ratio of the solute to the first solubilizer is 1:1 to 20.

11. The method according to claim 10,
    wherein the weight ratio of the solute to the first solubilizer is 1:2 to 20.

12. The method according to claim 10,
    wherein the composition further comprises a pH adjuster.

13. The method skin according to claim 12,
    wherein the pH adjuster is at least one of potassium hydroxide (KOH), calcium hydroxide (Ca(OH)$_2$), sodium carbonate (Na$_2$CO$_3$), potassium carbonate (K$_2$CO$_3$), sodium bicarbonate (NaHCO$_3$), lithium hydroxide (LiOH), citric acid, lactic acid, 2-aminobutanol, acetic acid, acetyl mandelic acid, adipic acid, aluminum hydroxide oxide, aluminum triformate, aminoethyl propanediol, aminomethyl propanediol, aminomethyl propanol, aminopropanediol, ammonia, ammonium bicarbonate, ammonium carbamate, ammonium carbonate, ammonium glycolate, ammonium hydroxide, ammonium phosphate, ascorbic acid, azelaic acid, babassu acid, benzylic acid, benzoic acid, bis-hydroxyethyl tromethamine, butyl diethanolamine, butylethanolamine, calcium citrate, calcium dihydrogen phosphate, calcium glycinate, calcium oxide, camphor sulfonic acid, chloroacetic acid, copper glycinate, dibutyl ethanolamine, diethanolamine, diethanolamine bisulfate, diisopropanolamine, diisopropylamine, dimethyl isopropanolamine, dimethyl MEA, dioleoyl edetolmonium methosulfate, dioleyl phosphate, dipotassium phosphate, dipropylenetriamine, disodium fumarate, disodium phosphate, disodium pyrophosphate, disodium tartrate, ethanolamine, ethanolamine HCl, ethyl ethanolamine, formic acid, fumaric acid, galacturonic acid, geranic acid, glucoheptonic acid, glucosamine HCl, glucuronic acid, glutaric acid, glycolic acid, glyoxylic acid, guanidine carbonate, hydrobromic acid, hydrochloric acid, imidazole, isopropanolamine, isopropylamine, ketoglutaric acid, lactobionic acid, lithium carbonate, magnesium carbonate, magnesium carbonate hydroxide, magnesium glycinate, magnesium hydroxide, magnesium oxide, maleic acid, malic acid, malonic acid, maltobionic acid, metaphosphoric acid, methoxy PEG-100/polyepsilon caprolactone ethylhexanoate, methoxy PEG-100/polyepsilon caprolactone palmitate, methoxy PEG-114/polyepsilon caprolactone, methylethanolamine, methylglucamine, morpholine, morpholinopropane sulfonic acid, oxalic acid, p-anisic acid, pentapotassium triphosphate, pentasodium triphosphate, phenolsulfonphthalein, phosphoric acid, potassium bicarbonate, potassium biphthalate, potassium borate, potassium citrate, potassium magnesium aspartate, potassium oxide, potassium phosphate, potassium tartrate, propionic acid, quinic acid, ribonic acid, sebacic acid, sesquiethoxytriethanolamine, sodium aluminate, sodium anisate, sodium arachidate, sodium bisulfate, sodium borate, sodium calcium boron phosphate, sodium calcium copper phosphate, sodium calcium zinc phosphate, sodium cinnamate, sodium citrate, sodium cyanate, sodium fumarate, sodium glycolate, sodium hydroxide, sodium oxide, sodium sesquicarbonate, sodium silicate, sodium succinate, sodium trimetaphosphate, sodium tungstate antimonate, strontium hydroxide, succinic acid, sulfonated styrene/DVB crosspolymer, sulfuric acid, tartaric acid, TEA-diricinoleate/IPDI copolymer, tetrapotassium pyrophosphate, tetrasodium pyrophosphate, triethanolamine, triisopropanolamine, trisodium phosphate, trisodium sulfosuccinate, tromethamine, vinegar, zinc carbonate hydroxide, zinc glycinate, or zinc magnesium aspartate.

14. The method according to claim 10,
wherein, when the composition has a pH of 2 or higher, the weight ratio of the solute to the first solubilizer is 1:1 to 20.

15. The method according to claim 14,
wherein, when the composition has a pH of 2 to 10, the weight ratio of the solute to the first solubilizer is 1:4 to 12.

16. The method according to claim 10,
wherein the content of the solute is 0.01 to 20% by weight based on the total weight of the composition.

17. The method according to claim 10,
wherein the composition comprises a second solubilizer which is at least one selected from the group consisting of xanthan gum, hydroxypropyl methylcellulose, sodium polyacrylate, sodium magnesium silicate, hydroxyethyl acrylate/sodium acryloyldimethyl taurate copolymer, polyacrylate-13/polyisobutene/polysorbate-20, PEG-240/HDI copolymer bis-decyltetraceth-20 ether and magnesium aluminum silicate.

18. The method according to claim 10,
wherein the composition is a pharmaceutical or cosmetic composition.

* * * * *